United States Patent [19]

Alt et al.

[11] 4,013,448
[45] Mar. 22, 1977

[54] 1,2,4-TRIAZOL-5-YL SULFAMIDES
[75] Inventors: Gerhard H. Alt, Creve Coeur; James A. Kloek, Overland, both of Md.
[73] Assignee: Monsanto Company, St. Louis, Mo.
[22] Filed: Dec. 29, 1975
[21] Appl. No.: 645,187
[52] U.S. Cl. .............................. 71/92; 260/308 R
[51] Int. Cl.² ............... A01N 9/16; C07D 249/14; A01N 9/22
[58] Field of Search ............... 260/308 R; 71/92
[56] References Cited
UNITED STATES PATENTS

| | | | |
|---|---|---|---|
| 3,144,460 | 8/1964 | Hosler et al. | 260/308 R |
| 3,709,677 | 1/1973 | Houlihan | 71/92 |

OTHER PUBLICATIONS

Deutsche Gold– und Silber–Scheideanstaet vorm. Roessler, *Chem. Abstracts*, vol. 62, col. 9708e (1965).

*Primary Examiner*—Alton D. Rollins
*Attorney, Agent, or Firm*—Richard H. Shear; Donald W. Peterson

[57] ABSTRACT

A compound having the formula

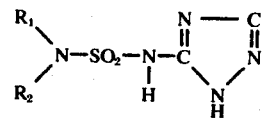

wherein $R_1$ and $R_2$ are independently hydrogen or lower alkyl, said compound possessing herbicidal properties.

9 Claims, No Drawings

1,2,4-TRIAZOL-5-YL SULFAMIDES

This invention relates to novel 1,2,4-triazol-5-yl sulfamides having the formula $$\begin{array}{c} R_1 \\ \diagdown \\ N-SO_2N-C \\ \diagup \quad\quad\quad | \quad \diagdown \\ R_2 \quad\quad H \quad\quad N \\ \quad\quad\quad\quad | \\ \quad\quad\quad\quad H \end{array} \begin{array}{c} N == C-H \\ || \\ \diagup \\ N \end{array} \quad (A)$$

wherein $R_1$ and $R_2$ are independently selected from the group consisting of hydrogen and lower alkyl.

The term "lower" alkyl is used herein to encompass those alkyl groups having from 1 to 4 carbon atoms, inclusive.

The 1,2,4-triazol-5-yl sulfamides of the above formula are useful as herbicides in preventing the growth of undesirable plants.

Generally, the 1,2,4-triazol-5-yl sulfamides are prepared by adding alkyl sulfamoyl chloride to a solution of 3-aminotriazole, triethylamine and nitromethane. The resulting solution is stirred until the reaction is complete. The solvent may then be removed in vacuo and the product isolated by crystallization or chromatography followed by crystallization.

The following examples are presented to more particularly illustrate the preparation of the novel compounds and are not intended as a restriction of the scope of the invention. Temperatures are understood to be degrees Centigrade (°C).

EXAMPLE 1

Preparation of N-t-butyl-N'-(1H-1,2,4-triazol-5-yl) Sulfamide

To a stirred solution of 1 molar equivalent of 3-aminotriazole and one molar equivalent of triethylamine in a convenient amount of nitromethane was added one molar equivalent of N-t-butyl sulfamoyl chloride. The resulting mixture was stirred 18 hours at room temperature, then concentrated on a rotary evaporator. The resulting solid was recrystallized from isopropanol to afford compound 1 below as a crystalline solid: m.p. 179°–180°.

Calc'd. for $C_6H_{13}N_5O_2S$: C, 32.87; H, 5.88; N, 31.94. Found: C, 32.88; H, 6.03; N, 31.76.

$$\begin{array}{c} CH_3 \quad CH_3 \\ \diagdown \diagup \\ C \\ \diagup \diagdown \\ CH_3 \quad NSO_2-N-C \\ \quad\quad\quad | \quad H \\ \quad\quad\quad H \end{array} \begin{array}{c} N == C-H \\ || \quad || \\ N \\ | \\ H \end{array} \quad (1)$$

EXAMPLE 2

Preparation of N,N-Dimethyl-N'-(1H-1,2,4-triazol-5-yl)Sulfamide

To prepare Compound 2 below the procedure of Example 1 was followed except that N,N-dimethyl sulfamoyl chloride was used in lieu of N-t-butyl sulfamoyl chloride.

$$\begin{array}{c} CH_3 \\ \diagdown \\ NSO_2N-C \\ \diagup \quad\quad | \quad \diagdown \\ CH_3 \quad H \quad\quad N \\ \quad\quad\quad | \\ \quad\quad\quad H \end{array} \begin{array}{c} N == C-H \\ || \\ \diagup \\ N \end{array} \quad (2)$$

m.p. 88°–89°.

Calc'd for $C_4H_9N_5O_2S$: C, 25.13; H, 4.24; N, 36.63. Found: C, 25.43; H, 4.67; N, 36.57.

In accordance with the present invention, the 1,2,4-triazol-5-yl sulfamides of the foregoing formula (A) possess herbicidal properties, especially post-emergent herbicidal properties. Such herbicidal properties were determined in accordance with the following tests. The procedure of test A was used to determine pre-emergent herbicidal properties while the procedure of test B was used to determine post-emergent herbicidal properties.

TEST A

A good grade of top soil was placed in aluminum pans and compacted to a depth of three-eighths to one-half inch from the top of the pan. On the top of the soil was placed a pre-determined number of seeds or vegetative propagules of various spectra of plant species. The soil required to level fill the pans after seeding or adding vegetative propagules was weighed into a pan. A known amount of the active ingredient applied in a solvent or as a wettable powder and the soil were thoroughly mixed, and used as a cover layer for prepared pans. After treatment the pans were moved into a greenhouse bench where they were watered from below as needed to give adequate moisture for germination and growth.

Unless noted otherwise, approximately 28 days after seeding and treating, the plants were observed to determine all deviations from the normal growth habit and the results recorded. A herbicidal rating code was used to signify the extent of phytotoxicity of each species. The ratings are defined as follows:

| % Control | Rating |
| --- | --- |
| 0–24 | 0 |
| 25–49 | 1 |
| 50–74 | 2 |
| 75–100 | 3 |

Test B

The post-emergent tests were conducted as follows. The active ingredients are applied in spray form to two or three-week old specimens of various spectra of plant species. The spray, a solution or wettable powder suspension containing the appropriate rate of active ingredient to give the desired test rate and a surfactant, is applied to the plants. The treated plants are placed in a greenhouse and unless otherwise noted approximately four weeks later the effects are observed and recorded. The results are shown in the tables below in which the post-emergent herbicidal rating code is as follows:

| % Control | Rating |
| --- | --- |
| 0–24 | 0 |
| 25–49 | 1 |

| % Control | Rating |
|---|---|
| 50-74 | 2 |
| 75-99 | 3 |
| 100 | 4 |

The plant species utilized in these tests are identified by letter in accordance with the following legend:

| | |
|---|---|
| A Canada Thistle | K Barnyard grass |
| B Cocklebur | L Soybean |
| C Velvetleaf | M Sugar Beet |
| D Morningglory | N Wheat |
| E Lambsquarter | O Rice |
| F Smartweed | P Sorghum |
| G Nutsedge | Q Wild Buckwheat |
| H Quackgrass | R Hemp sesbania |
| I Johnsongrass | S Panicum spp |
| J Bromus tectorum | T Crabgrass |

Tables I, II, III and IV summarize the results of Tests A and B on the various spectra of plant species.

TABLE I

Results of Test A in Spectrum 1

| Compound | Rate lb/acre (kg/ha) | A | B | C | D | E | F | G | H | I | J | K |
|---|---|---|---|---|---|---|---|---|---|---|---|---|
| 1 | 5.0* (5.6) | 3 | 0 | 0 | 0 | 3 | 0 | 0 | 3 | 0 | 0 | 0 |
| 2 | 10.0* (11.2) | 0 | 0 | 0 | 0 | 1 | 0 | 0 | 2 | 0 | 1 | 0 |
| | 10.0 (11.2) | 2 | 0 | 1 | 0 | 1 | 0 | 0 | 3 | 0 | 2 | 0 |

TABLE II

Results of Test A on Spectrum 2

| Compound | Rate lb/acre (kg/ha) | L | M | N | O | P | B | Q | D | R E | F | C | J | S | K | T |
|---|---|---|---|---|---|---|---|---|---|---|---|---|---|---|---|---|
| 1 | 5.0+ (5.6) | 3 | 3 | 3 | 2 | 0 | 0 | 1 | 0 | 3 | 1 | 0 | 2 | 3 | 3 | 2 | 3 |
| | 5.0 (5.6) | 3 | 3 | 3 | 2 | 0 | 0 | 1 | 0 | 3 | 1 | 0 | 2 | 3 | 3 | 2 | 3 |

TABLE III

Results of Test B on Spectrum 1

| Compound | Rate lb/acre (kg/ha) | A | B | C | D | E | F | G | H | I | J | K |
|---|---|---|---|---|---|---|---|---|---|---|---|---|
| 1 | 4.0* (4.48) | 2 | 2 | 2 | 2 | 3 | 2 | 0 | 3 | 2 | 3 | 3 |
| | 4.0 (4.48) | 3 | 3 | 3 | 2 | 4 | 3 | 1 | 3 | 2 | 3 | 3 |
| | 5.0* (5.6) | 2 | 0 | 2 | 0 | 1 | 0 | 0 | 2 | 1 | 2 | 2 |
| | 5.0 (5.6) | 3 | 0 | 3 | 0 | 0 | 0 | 0 | 2 | 0 | 3 | 1 |

TABLE IV

Results of Test B on Spectrum 2

| Compound | Rate lb/acre (kg/ha) | L | M | N | O | P | B | Q | D | R | E | F | C | J | S | K | T |
|---|---|---|---|---|---|---|---|---|---|---|---|---|---|---|---|---|---|
| 1 | 4.0* (4.48) | 3 | 2 | 3 | 1 | 2 | 2 | 2 | 3 | 2 | 2 | 2 | 2 | 2 | 2 | 2 | 3 |
| | 4.0 (4.48) | 3 | 3 | 3 | 3 | 2 | 3 | 3 | 3 | 3 | 3 | 2 | 3 | 3 | 4 | 3 | 3 |
| 2 | 5.0* (5.6) | 1 | 1 | 2 | 0 | 1 | 0 | 0 | 0 | 0 | 0 | 0 | 2 | 1 | 1 | 0 | 0 |

*Plants observed approximately 14 days after treatment.
+Plants observed approximately 21 days after treatment.

For the sake of brevity and simplicity, the term "active ingredient" has been used herein and is used hereinafter to describe the 1,2,4-triazol-5-yl sulfamides of Formula A.

In practicing the herbicidal methods of this invention, the active ingredients can be used alone or in combination with a material referred to in the art as an adjuvant in liquid or solid form. Herbicidal formulations are prepared by admixing the active ingredient with an adjuvant including diluents, extenders, carriers and conditioning agents to provide compositions in the form of finely-divided particulate solids, granules, pellets, solutions, dispersions or emulsions. Thus, the active ingredient can be used with an adjuvant such as a finely-divided particulate solid, a liquid of organic origin, water, a wetting agent, dispersing agent, an emulsifying agent or any suitable combination of these. The herbicidal formulations usually contain from about 0.01 to about 99 percent by weight of active ingredient.

Typical finely-divided solid carriers and inert solid extenders which can be used with the active ingredients include, for example, the talcs, natural and synthetic clays (e.g. kaolinites and attapulgite), pumice, silica, synthetic calcium and magnesium silicates, diatomaceous earth, quartz, Fuller's earth, salt, sulfur, powdered cork, powdered wood, ground corn cobs, walnut flour, chalk, tobacco dust, charcoal, volcanic ash, cottonseed hulls, wheat flour, soybean flour, tripoli and the like. Typical liquid diluents include for example: petroleum fractions such as kerosene, hexane, xylene, benzene, Diesel oil, toluene, acetone, ethylene dichloride, Stoddard solvent, alcohols such as propanol, glycols and the like.

Herbicidal formulations, particularly liquids and wettable particles, usually contain as a conditioning agent one or more surface-active agents in amounts sufficient to render a given composition readily dispersible in water or in oil. By the term "surface-active agent" it is understood that wetting agents, dispersing agents, suspending agents and emulsifying agents are included therein.

Specific surface-active agents which can be used in the herbicidal formulations of this invention are set out, for example, in Searle U.S. Pat. Nos. 2,426,417; Todd 2,655,447; Jones 2,412,510 and Lenher 2,139,276. In general, less than 50 parts by weight of the surface-active agent is present per 100 parts by weight of phytotoxic formulation.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, polyoxyethylene derivatives of alkylphenols (particularly isooctylphenol and nonylphenyl) and polyoxyethylene derivatives of the mono-higher fatty esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) laurates.

Wettable powder formulations usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total formulation. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely divided particles. The resulting concentrated aqueous suspension is characterized by its extremely small particle size, so that when diluted and sprayed coverage is very uniform.

Dusts are dense finely divided particulate formulations which are intended for application to the soil in dry form. Dusts are characterized by their free-flowing and rapid settling properties so that they are not readily wind-borne to areas where they are of no value. Dusts contain primarily an active ingredient and a dense, free-flowing finely divided particulate extender. However, their performance is sometimes aided by the inclusion of a wetting agent such as those listed hereinbefore under wettable powder compositions and convenience is manufacture frequently demands the inclusion of an inert, absorptive grinding aid. Suitable classes of grinding aids are natural clays, diatomaceous earth and synthetic minerals derived from silica and silicate. Preferred grinding aids include attapulgite clay, diatomaceous silica, synthetic fine silica and synthetic calcium and magnesium silicates.

The inert finely divided solid extender for the dusts can be either of vegetable or mineral origin. The solid extenders are characterized by possessing relatively low surface areas and are poor in liquid absorption. Suitable inert solid extenders for herbicidal dusts include micaceous talcs, pyrophyllite, dense kaolin clays, ground calcium phosphate rock and phyllite, and tobacco dust. The dusts usually contain from about 0.5 to 95 parts active ingredient, 0 to 50 parts grinding aid, 0 to 50 parts wetting agent and 5 to 99.5 parts dense solid extender, all parts being by weight and based on the total weight of the dust.

The wettable powders described above may also be used in the preparation of dusts. While such wettable powders could be used directly in the dust form, it is more advantageous to dilute them by blending with the dense dust diluent. In this manner, dispersing agents, corrosion inhibitors, and anti-foam agents may also be found as components of a dust.

Emulsifiable oil formulations are usually solutions of active ingredient in water-immiscible or partially water-immiscible solvents together with a surface-active agent. Suitable solvents for the active ingredient of this invention include hydrocarbons and water-immiscible ethers, esters or ketones. Suitable surface-active agents are anionic, cationic and non-ionic such as alkyl aryl polyethoxy alcohols, polyethylene sorbitol or sorbitan fatty acid esters, polyethylene glycol fatty acids, fatty alkyllol amide condensates, amine salts of fatty alcohol sulfates together with long chain alcohols and oil soluble petroleum sulfonates or mixtures thereof. The emulsifiable oil formulations generally contain from about 5 to 95 parts active ingredient, about 1 to 50 parts surface active agent and about 4 to 94 parts solvent, all parts being by weight based on the total weight of the emulsifiable oil.

Granules are physically stable particulate formulations comprising active ingredient adhering to or distributed through a basic matrix of an inert, finely divided particulate extender. In order to aid leaching of the active ingredient from the particulate, a surface active agent such as those listed hereinbefore under wettable powders can be present in the composition. Natural clays, pyrophyllites, illite and vermiculite are examples of operable classes of particulate mineral estenders. The preferred extenders are the porous, absorptive, pre-formed particles such as preformed and screened particulate attapulgite or heat expanded, particulate vermiculite, and the finely divided clays such as kaolin clays, hydrated attapulgite or bentonitic clays. These extenders are sprayed or blended with the active ingredient to form the herbicidal formulations.

The mineral particles which are used in the herbicidal formulations usually have a size range of 10 to 100 mesh, but preferably such that a large majority of the particles have from 14 to 60 mesh with the optimum size being from 20 to 40 mesh. Clay having substantially all particles between 14 and 80 mesh and at least about 80 percent between 20 and 40 mesh is particularly preferred for use in the herbicidal formulations. The term "mesh" as used herein means U.S. Sieve Series.

The granular herbicidal formulations generally contain from about 5 parts to about 30 parts by weight of active ingredient per 100 parts by weight of clay and 0 to about 5 parts by weight of surface-active agent per 100 parts by weight of particulate clay. The preferred granular formulations contain from about 10 parts to about 25 parts by weight of active ingredient per 100 parts by weight of clay.

The herbicidal formulations can also contain other additaments, for example, fertilizers, plant growth regulants, pesticides and the like used as adjuvant or in combination with any of the above-described adjuvants.

When operating in accordance with the present invention, effective amounts of the active ingredients are applied to the plant system. By application to the plant system is meant the application of the active ingredient in or on soil or plant growth media and/or applied to above ground portions of plants in any convenient fashion. Application to the soil or growth media can be carried out by simply mixing with the soil, by applying to the surface of the soil and thereafter dragging or discing into the soil to the desired depth, or by employing a liquid carrier to accomplish the penetration and impregnation. The application of liquid and particulate solid herbicidal formulations to the surface of soil or to above ground portions of plants can be carried out by conventional methods, e.g. powder dusters, boom and hand sprayers and spray dusters. The formulations can also be applied from airplanes as a dust or a spray because of their effectiveness at low dosages. In a further method, the distribution of the active ingredients in soil can be carried out by admixture with the water employed to irrigate the soil. In such procedures, the amount of water can be varied with the porosity and water holding capacity of the soil to obtain the desired depth of distribution of the active ingredients.

The application of an effective amount of the active ingredients of this invention to the soil or growth media and/or plant is very important for the practice of one embodiment of the present invention. The exact amount of active ingredient to be employed is dependent upon such factors as the plant species and stage of development thereof, the specific soil and depth at which the active ingredients are distributed in the soil and the amount of rainfall as well as the specific active ingredient employed. In foliar treatment for the modification of vegetative growth, the active ingredients are applied in amounts of from about one pound up to about 25 or more pounds per acre. In applications to soil for the modification of the germination or subsequent growth of seeds or vegetative propagules or growth of established vegetation, the active ingredients are applied in amounts from about 1 to about 50 or more pounds per acre. It is believed that one skilled in the art can readily determine from the teachings of this specification the general procedure for any application.

In summary, in general the active ingredients may be formulated with the active ingredient in minor or major proportions in accordance with the table below:

| Type of Formulation | Concentration of Active Ingredient |
| --- | --- |
| 1. Granules of relatively large particle size | 5 to 50% |
| 2. Powdery dusts | 2 to 90% |
| 3. Wettable powders | 2 to 90% |
| 4. Emulsifiable concentrates | 5 to 95% |
| 5. Solutions | .01 to 95% |
| 6. One of the less common types of formulations depending on the desired mode of application. | .01 to 95% |

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

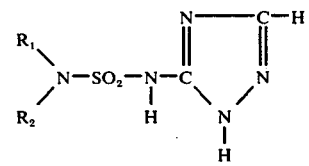

wherein $R_1$ and $R_2$ are independently selected from the group consisting of hydrogen and lower alkyl.

2. A compound according to claim 1 wherein $R_1$ is t-butyl and $R_2$ is hydrogen.

3. A compound according to claim 1 wherein $R_1$ and $R_2$ are methyl.

4. A method of preventing the growth of undesirable plants which comprises applying to the plant system a herbicidally effective amount of a compound having the formula

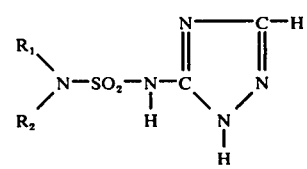

wherein $R_1$ and $R_2$ are independently selected from the group consisting of hydrogen and lower alkyl.

5. A method according to claim 4 wherein $R_1$ is t-butyl and $R_2$ is hydrogen.

6. A method according to claim 4 wherein $R_1$ and $R_2$ are methyl.

7. A herbicidal composition comprising a herbicidal adjuvant and a herbicidally effective amount of a compound having the formula

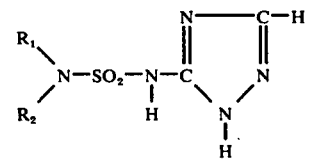

wherein $R_1$ and $R_2$ are independently selected from the group consisting of hydrogen and lower alkyl.

8. A composition according to claim 7 wherein $R_1$ is t-butyl and $R_2$ is hydrogen.

9. A composition according to claim 7 wherein $R_1$ and $R_2$ are methyl.

* * * * *